US006221617B1

(12) United States Patent
Heinrich et al.

(10) Patent No.: US 6,221,617 B1
(45) Date of Patent: Apr. 24, 2001

(54) BIOASSAY FOR GROWTH HORMONE RELEASING HORMONE

(76) Inventors: Julie Heinrich, 3000 Jackson Dr., Lincoln, NE (US) 68502; H. Edward Grotjan, 18 Ravens Pointe, Lake St. Louis, MO (US) 63367; Fred W. Wagner, Rte. 1, Box 778, Walton, NE (US) 68451; Yuannan Xia, 2354 N. 44th St., Apt. 19, Lincoln, NE (US) 68504

( * ) Notice: Subject to any disclaimer, the term of this patent is extended or adjusted under 35 U.S.C. 154(b) by 0 days.

(21) Appl. No.: 08/986,049

(22) Filed: Dec. 5, 1997

Related U.S. Application Data

(60) Provisional application No. 60/032,928, filed on Dec. 6, 1996.

(51) Int. Cl.[7] ............................ G01N 33/50; G01N 33/53

(52) U.S. Cl. ........................... 435/7.2; 435/7.21; 435/7.6; 435/8; 435/21; 435/325

(58) Field of Search ............................ 435/7.2, 6, 7.21, 435/8, 7.6, 21, 325, 366, 252.3; 436/501

(56) References Cited

U.S. PATENT DOCUMENTS

| 4,870,054 | 9/1989 | Recker .................................. 514/12 |
| 5,118,666 | 6/1992 | Habener ................................ 514/12 |
| 5,401,629 | 3/1995 | Harpold et al. .......................... 435/6 |
| 5,436,128 | 7/1995 | Harpold et al. .......................... 435/6 |
| 5,583,010 | 12/1996 | Baumbach et al. ................. 435/69.1 |
| 5,644,046 | 7/1997 | Thorner et al. ..................... 536/23.5 |

FOREIGN PATENT DOCUMENTS 0 576 988 A1   1/1994  (EP) .

OTHER PUBLICATIONS

Albanese, C. et al., *Molecular and Cellular Endocrinology*, 101:211–219 "Development of a bioassay for FSH using a recombinant human FSH receptor and a cAMP responsive luciferase reporting gene".
Artelt et al., 1991, *Gene* 99(2):249–254 "The prokaryotic neomycin–resistance–encoding gene acts as a transcriptional silencer in eukaryotic cells".
Berger et al., 1988, *Gene* 66:1–10 "Secreted placental alkaline phosphatase: A powerful new quantitative indicator of gene expression in eukaryotic cells".
Bohlen et al., 1983, *Biochemical and Biophysical Research Communications* 116:726 "Isolation and characterization of the porcine growth hormone releasing factor".
Bronstein, I. et al., 1994, *Analytical Biochemistry*, 219:169–181 "Chemiluminescent and bioluminescent reporter gene assays".
Culler et al., 1992, *Methods in Enzymology* 216:362–368 "Secreted placental alkaline phosphatase as a eukaryotic reporter gene".

De la Luna et al., 1988, *Gene* 62:121–126 "Efficient transformation of mammalian cells with constructs containing a puromycin–resistance marker".
De Lean et al., 1978, *American Journal of Physiology* 235(2):E97–E102 "Simultaneous analysis of families of sigmoidal curves: Application to bioassay, radioligand assay, and physiological dose–response curves".
Eggermont, J. et al. 1993), *The EMBO Journal*, 12:2530–2548 "Poly(A) signals and transcriptional pause sites combine to prevent interference between RNA polymerase II promoters".
Gaylinn, B.D. et al. (1993), *Molecular Endocrinology*, 7:77–84 "Human anterior pituitary receptor for growth hormone–releasing hormone".
Frank, Julie A., 1996, Thesis "Bioassay for Growth Hormone Releasign Hormone (GHRH) Utilizing a Cyclic Amp––Responsive Alkaline Phosphatease Reporter System and a Recombinant GHRH Receptor".
Grotjan et al., 1977, *Computers in Biology and Medicine* 7:159–163 "Radioimmunoassay and bioassay data processing using a logistic curve fitting routine adapted to a desk top computer".
Hsiung et al., 1993, *Neuropeptides* 25:1–10 "Structure and functional expression of a complementary DNA for porcine growth hormone–releasing hormone receptor".
Jameson et al., 1988, *Journal of Biological Chemistry*, 263(20):9879–9886 "The gonadotropin α–gene contains multiple protein binding domains that interact to modulate basal and cAMP–responsive transcription".
Jia, X. et al. (1993), *Biology of Reproduction*, 49:1310–1316 "Luminescence luteinizing hormone/choriogonadotropin (LH/CG) bioassay: Measurement of serum bioactive LH/CG during early pregnancy in human and macaque".
Mayo et al., 1992, *Molecular Endocrinology* 6:1734–1744 "Molecular cloning and expression of a pituitary–specific receptor for growth hormone–releasing hormone".
ATCC Cell Lines and Hybridomas, 8th edition, Hay et al., eds., p. 149, 1994.*
Srivastava et al. Endocrinology 136:1502–1508, Apr. 1995.*

* cited by examiner

*Primary Examiner*—Elizabeth Kemmerer
(74) *Attorney, Agent, or Firm*—Foley & Lardner

(57) ABSTRACT

A method and recombinant assay cell for detecting growth hormone releasing hormone (GHRH) in a sample, the method includes exposing a recombinant cell to the sample and measuring transcription of a reporter gene. A suitable recombinant cell includes a reporter gene operatively connected to a cAMP-responsive promoter and a GHRH-responsive protein whose binding to GHRH induces the production of cAMP. GHRH present in an assay sample results in the GHRH-responsive protein activating the production of cAMP, which then activates the c-AMP-responsive promoter to express the reporter protein. The amount of reporter protein produced is quantitatively correlated to the amount of GHRH in the sample. In one embodiment, the protein is a cell surface receptor for GHRH.

16 Claims, 9 Drawing Sheets pSEAP-Basic phα180SEAPpur

EVALUATION OF THE cAMP-RESPONSIVE SECRETED ALKALINE PHOSPHATASE CONSTRUCT, phα180SEAP, AS A REPORTER SYSTEM.

EVALUATION OF cAMP IN
RESPONSE TO GHRH

GHRH-SEAP REPORTER BIOASSAY

SEQUENCE LISTING

<160> NUMBER OF SEQ ID NOS: 2

<210> SEQ ID NO: 1
<211> LENGTH: 35
<212> TYPE: DNA
<213> ORGANISM: Synthetic Primer

<400> SEQUENCE: 1
taggctcttc cagccagctg tggaatgtgt gtcag                35

<210> SEQ ID NO: 2
<211> LENGTH: 33
<212> TYPE: DNA
<213> ORGANISM: Synthetic Primer

<400> SEQUENCE: 2
attaactcga gggcagcagg gtgttgggcc ctt                  33

BIOASSAY FOR GROWTH HORMONE RELEASING HORMONE

This application claims priority under 35 U.S.C. 119(e) to provisional application No. 60/032,928 filed Dec. 6, 1996.

TECHNICAL FIELD

This invention relates to assays for measuring the biological activity of an extracellular signal. More specifically, this invention relates to a bioassay for growth hormone releasing hormone (GHRH).

BACKGROUND OF THE INVENTION

Growth hormone releasing hormone (GHRH) is a peptide secreted by the hypothalamus. Normally, GHRH stimulates pituitary growth hormone release. The presence and activity of GHRH is therefore very important, particularly in normal growth and childhood development.

GHRH is also useful for testing pituitary function. Doses of GHRH can be used to stimulate pituitary secretion of growth hormone. If GHRH does not stimulate the pituitary to secrete growth hormone, this tends to indicate that the pituitary gland is not functioning properly.

GHRH can also be used to treat postmenopausal osteoporosis. Administration of GHRH can result in a reversal in bone mass loss in postmenopausal patients.

Because GHRH has many medical applications, it is highly desirable to be able to detect the presence or absence of GHRH in a sample or to qualitatively or quantitatively measure the activity of GHRH in a convenient, reliable manner.

Primary cultures of rat pituitary cells are typically used in a radioimmunoassay to asses the biological activity of GHRH. However, this radioimmunoassay is costly, time consuming and requires animals and radioactive materials.

A bioassay that would reduce the amount of time needed to detect GHRH in a sample would therefore be desirable. Additionally, it would be preferable if the bioassay did not require live animals, radioactive materials or specific antibodies.

SUMMARY OF THE INVENTION

This invention is directed to an in vitro bioassay method for detecting growth hormone releasing hormone (GHRH) in a sample. The method includes exposing a recombinant assay cell responsive to GHRH to a sample and measuring expression of a reporter gene whose expression is correlated to the concentration of GHRH in the sample.

A second aspect of the invention is directed to a recombinant assay cell useful for detecting GHRH in a sample. A suitable recombinant assay cell expresses a protein that is responsive to GHRH, e.g., a GHRH receptor which, upon activation by GHRH, causes the production of cAMP. The recombinant assay cell also expresses a reporter gene operatively connected to a cAMP-responsive promoter.

In the assay method of the invention, GHRH present in a sample activates the GHRH responsive protein, which then causes the production of cAMP. cAMP induces the expression of the reporter gene, and a signal generated by the reporter protein is quantitatively correlated with the concentration of GHRH in the sample.

DETAILED DESCRIPTION OF THE INVENTION

Figure 1:
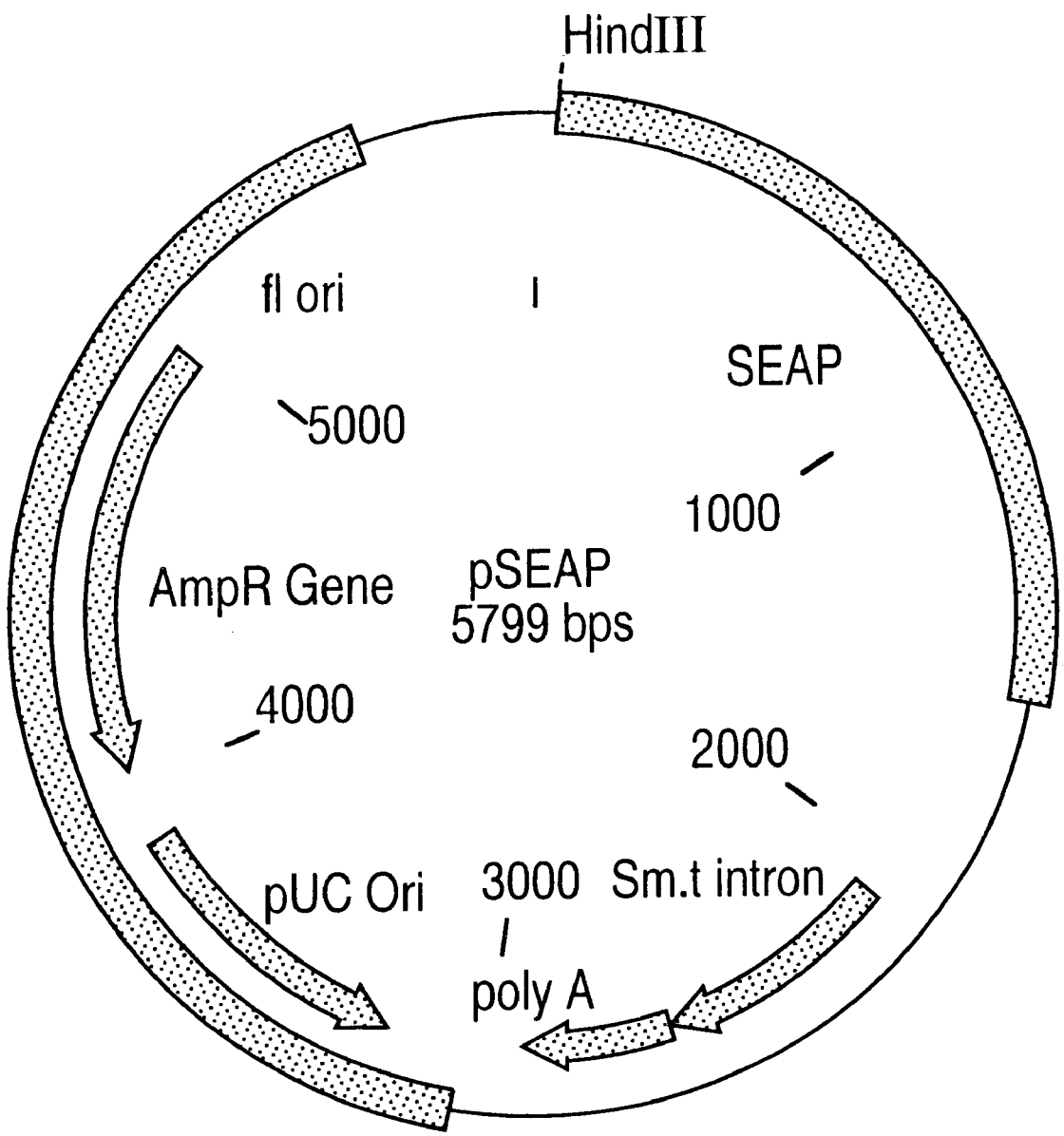
FIG. 1 is a plasmid map of pSEAP.

The present invention is directed to an assay for detecting growth hormone releasing hormone (GHRH) in a sample. For the purposes of this invention, "detecting" GHRH can include, but is not limited to, determining the presence or absence of GHRH in a sample, qualitatively or quantitatively measuring the biological activity of GHRH in a sample. It should be noted that, because one of the purposes of the assay is the determination of whether or not GHRH is present in a sample, the sample may or may not contain GHRH. For the purposes of this invention, a "sample" includes, but is not limited to, body fluids such as whole blood, serum or plasma; secretions, such as sweat, tears or saliva; or pharmaceutical preparations, such as preparations for the treatment of osteoporosis or other growth disorders.

Generally, the method includes exposing a recombinant cell including a reporter gene to a sample and measuring expression of a reporter gene. The method is described in more detail below.

Growth Hormone Releasing Hormone

GHRH is an extracellular signal that exerts its effect on cells through a G-protein transmembrane signaling pathway. GHRH can bind to GHRH cell surface receptors and thereby activate G-proteins which, in turn, stimulate adenylate cyclase to produce cyclic AMP (cAMP) from ATP.

Cyclic AMP influences many cellular processes, typically by stimulating the activity of protein kinases that transfer terminal phosphate groups from ATP to specific amino acids on target proteins. Phosphorylation typically alters the activity of these proteins, either raising or lowering the activity. One example of a cellular process that can be influenced by the presence of cAMP is gene transcription. cAMP-responsive promoters are discussed in more detail below.

The assay of the present invention can be used to detect GHRH in a sample. For the purposes of the invention "GHRH" includes any molecule that is recognized by a GHRH-responsive protein. "Recognized by a GHRH-responsive protein" includes molecules that bind to the GHRH-responsive protein and thereby activate the protein. Binding of GHRH, or a biologically active analog thereof, to a GHRH-responsive protein results in the activation of adenylate cyclase and therefore, the production of cAMP, as described above. GHRH can include naturally occurring GHRH, recombinantly produced GHRH and biologically active analogs thereof. Naturally occurring GHRH can be derived from a wide variety of organisms, including, but not limited to, humans, or other animals. Biologically active analogs of GHRH include, but are not limited to, recombinantly produced GHRH, mutants, fragments, homologs, and allelic variants that bind to and activate the GHRH receptor. In one embodiment, the GHRH is GHRH(1–44NH$_2$).

GHRH Activity Assay

In the assay of the present invention, a recombinant cell is exposed to a sample which may or may not contain GHRH. To determine whether or not GHRH is present in the sample, to quantitate an amount of GHRH in the sample, or to measure the biological activity of GHRH, the expression of a reporter gene is measured.

The recombinant cell should be contacted with the sample for a time sufficient to activate the receptor, produce cAMP, induce transcription at the cAMP promoter, and produce the reporter protein, which may or may not be secreted from the cell. The time required for the assay will vary with the assay conditions and with the specific reporter protein, as known to those in the art. Generally, the cells will be incubated in the presence of sample for about 30 minutes to about 24 hours, after which time the reporter protein may be assayed.

Reporter gene expression can be measured using any known method. Although it is preferable that expression of the reporter gene be easily detected, the reporter gene can be any gene that expresses a detectable gene product such as RNA or protein. Therefore, expression of the gene product can be determined using Northern or Western blot assays. Alternatively, the gene product can be selected because it is easily measured. Examples of reporter genes encoding more easily measured gene products include, but are not limited to, alkaline phosphatase, luciferase, β-galactosidase, chloramphenicol acetyl transferase (CAT), lux operon, and green fluorescent protein (GFP). Alkaline phosphatase is especially preferred because the gene product is secreted and therefore very easily measured in the conditioned culture medium.

Preferably, the assay is run simultaneously with a second control assay wherein the control recombinant cell does not contain a GHRH-responsive protein. In a most preferred embodiment, the assay is run simultaneously with a control set of GHRH standards to generate a standard curve from which sample concentrations of GHRH can be quantitated.

Recombinant Cell

A suitable recombinant cell for use in the present invention includes a protein that is responsive to GHRH and a reporter gene whose expression is modulated by the binding of GHRH to the GHRH-responsive protein. "Modulated" can include up-regulation or down-regulation. Because binding of GHRH to a GHRH cell surface receptor results in the production of cAMP, it is preferred that expression of the reporter gene be modulated by cAMP. In one embodiment, the expression of the reporter gene can be modulated by a cAMP-responsive promoter. The recombinant cell can therefore be any cell expressing a GHRH-responsive protein that has been modified by the introduction of a reporter gene operatively connected to a transcriptional control element whose activity is affected by cAMP, for example, a cAMP-responsive promoter.

A heterologous DNA sequence encoding the reporter gene can be introduced into the recombinant cell by transient transfection or by stable transfection of a vector containing the DNA sequence. Numerous methods are know for introducing foreign DNA into a host cell.

In one embodiment, the host cell contains an endogenous DNA sequence encoding a GHRH-responsive protein. In this embodiment, a DNA sequence encoding the reporter gene is introduced into the cell. In another embodiment, the host cell may or may not contain an endogenous DNA sequence encoding a GHRH-responsive protein. In this embodiment, a heterologous DNA sequence encoding the reporter gene can be co-transfected with another heterologous DNA sequence encoding a GHRH responsive protein. Alternatively, the heterologous DNA sequence encoding the reporter gene can be included within a construct that also includes a heterologous DNA sequence encoding a GHRH-responsive protein. In the preferred embodiment, the recombinant assay cell stably expresses both the GHRH-responsive protein and the reporter gene.

Reporter Genes

The DNA encoding the reporter gene can be included within a DNA construct which further includes a transcriptional control sequence. A transcriptional control sequence can include regulatory elements such as promoter sequences, enhancer sequences, repressor sequences and the like. According to the present invention, the activity of the transcriptional control sequence can be affected by the binding of GHRH to a cell surface receptor due to the production of cAMP. Preferably, the transcriptional control element is a cAMP-responsive promoter, which in the presence of cAMP, modulates expression of the reporter. Most preferably, the cAMP-responsive promoter induces activity of the promoter in the presence of cAMP, resulting in expression of the reporter protein. Suitable cAMP-responsive promoters are known and include the promoter from human glycoprotein α subunit gene (hα promoter).

A promoter is a region of DNA upstream from the reporter gene with respect to the direction of transcription of the reporter gene and a transcription initiation site. It includes the RNA polymerase binding and transcription initiation sites and other regions such as repressor or activator protein binding sites.

The transcriptional control sequence is operatively linked to the DNA sequence encoding the reporter gene. Typically, the DNA sequences are included in a vector such as a plasmid, bacteriophage or yeast chromosome. The vector can also include other gene sequences such as a DNA sequence encoding the GHRH-responsive protein, resistance genes, enhancers or other regulatory elements such as terminators, polyadenylation sequences or nucleic acid sequences encoding signal peptides to direct the encoded protein to the cell surface.

GHRH Responsive Protein

A "GHRH responsive protein" is a protein that is capable of binding GHRH, wherein the activity of the GHRH-responsive protein is altered in response to the binding. In one embodiment, the protein can be a cell surface protein such as a GHRH receptor. In this embodiment, binding of GHRH to the GHRH-responsive protein results in the activation of a G-protein and the subsequent activation of adenylate cyclase to produce cAMP.

The recombinant cell used in the assay of the present invention may contain either an endogenous or heterologous DNA sequence encoding the GHRH-responsive protein. An endogenous DNA sequence is a DNA sequence that is naturally present in the genome of a cell such that the cell naturally expresses the GHRH-responsive protein. A heterologous DNA sequence includes a DNA sequence that does not occur naturally as part of the genome in which it is present. Additionally, a heterologous DNA sequence includes a DNA sequence in a location or locations in the genome that differs from the location(s) in which it occurs in nature. Methods for introducing heterologous DNA into a host cell are well know in the art and any such method may be used.

Suitable Host Cells

The reporter gene construct is transformed into a suitable host cell by known methods. A suitable host cell includes any transfectable cell that can express the desired GHRH-responsive protein and reporter gene product. The host cell may be selected such that it endogenously expresses the GHRH-responsive protein or the host cell may be genetically engineered to do so. Many such cells are known. Such cells include, but are not limited to, human fetal kidney cells, such as 293 cells.

EXAMPLES

The invention may be better understood with reference to the following examples, which are representative of some of the embodiments of the invention, and are not intended to limit the invention.

Materials and Methods

Cell Lines

Human embryonic kidney (293) cells (American Type Culture Collection, Rockville, Md.) were grown in DMEMlow glucose supplemented with 5% certified fetal calf serum, 100 U/ml penicillin, 100 ug/ml streptomycin sulfate and 0.25 ug/mL amphotericin B (Gibco/BRL Grand Island, N.Y.). A human fetal kidney 293 derived cell line expressing the porcine GHRH receptor (pGHRHr/293 cells) was obtained from American Cyanamid, Princeton, N.J. pGHRHr/293 cells were grown in DMEM-high glucose supplemented with 10% certified fetal calf serum, 2 mM L-glutamine, 100 U/ml penicillin, 100 ug/ml streptomycin sulfate, 0.25 ug/mL amphotericin B and 250 ug/ml G418 (Gibco/BRL Grand Island, N.Y.), the later antibiotic was used as a selectable marker for receptor expression.

Reagents and Hormones

Figure 2:
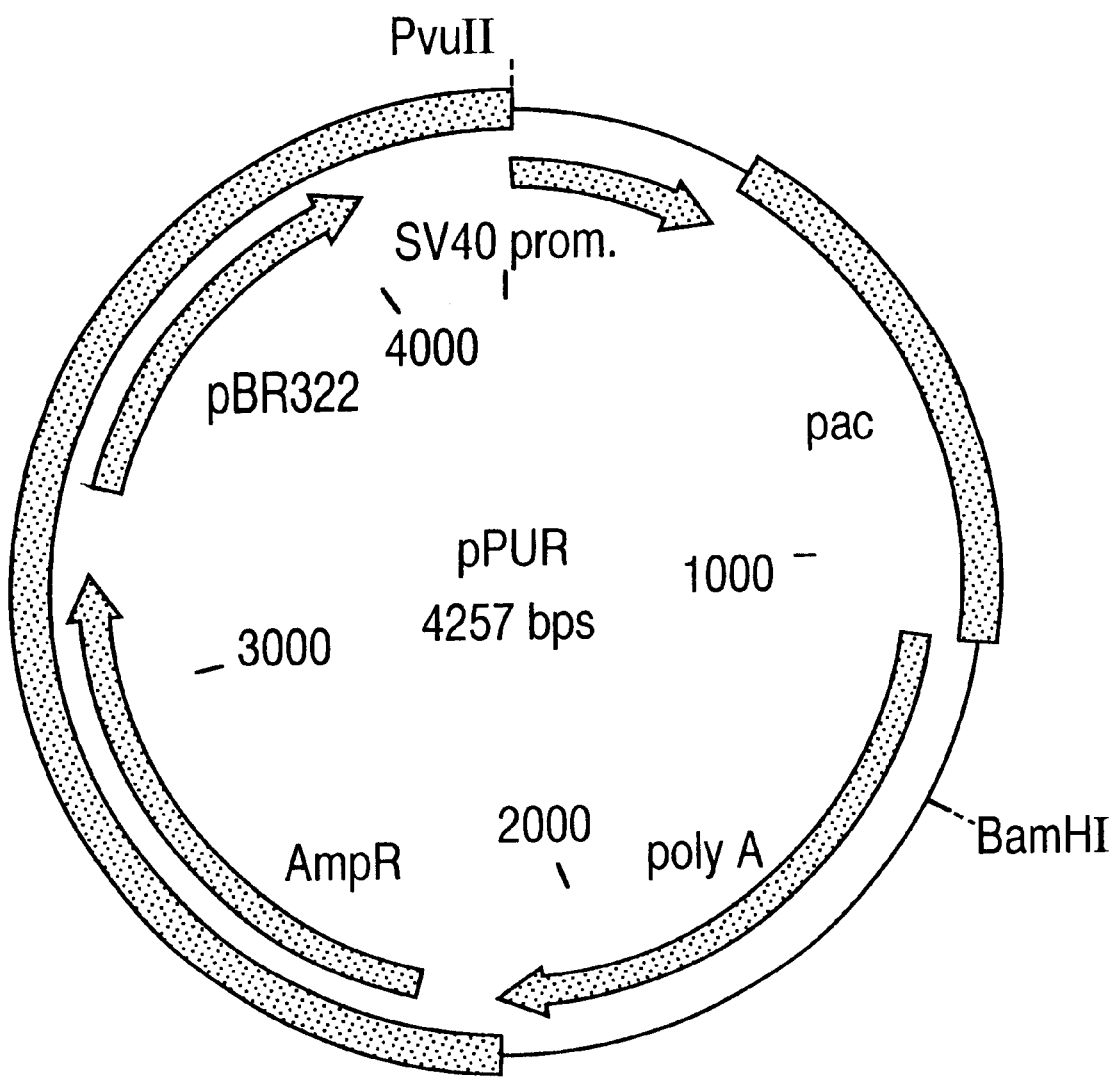
FIG. 2 is a plasmid map of pPur.

3-Isobutyl-1-methyl-xanthine was purchased from Aldrich (Milwaukee, Wis.). Bovine serum albumin was purchased from Sigma (St. Louis, Mo.). A plasmid containing a 230 bp cAMP-responsive promoter from the human glycoprotein alpha subunit gene inserted upstream from a luciferase reporter gene, phα180A3Luc, was obtained from Dr. J. Larry Jameson's laboratory at Northwestern University Medical School (Albanese, et al., 1994). An alkaline phosphatase reporter construct lacking a eukaryotic promoter or enhancer sequence, pSEAP-Basic (see FIG. 1), was purchased from Clontech (Palo Alto, Calif.). A plasmid containing a cDNA for puromycin acetyl transferase (pac) which confers resistance to puromycin, pPur (FIG. 2), and the Great Escape Chemiluminescent Detection kit were purchased from Clontech (Palo Alto, Calif.). Restriction enzymes were purchased from Promega (Madison, Wis.). High fidelity rTth DNA polymerase was purchased from Perkin Elmer (Norwalk, Conn.). Lipofectin was purchased from Gibco/BRL (Grand Island, N.Y.). Oligonucleotide primers were synthesized by Gibco/BRL (Grand Island, N.Y.) or Genosys (The Woodlands, Tex.). Biotrak Rat Growth Hormone Radioimmunoassay kits and Biotrak cAMP Elisa kits were purchased from Amersham (Arlington Heights, Ill.). Reagents for the rat primary pituitary bioassay included: Gey's (GBSS) media, non essential amino acids, DMEM (high glucose), fetal calf serum, sodium pyruvate, fungizone, antibiotic-antimycotic, Hepes buffer, and horse serum from Gibco/BRL (Grand Island, N.Y.); DNase I, bovine serum albumin, dexamethasone and 3,3',5-triiodo-$_L$-thyronine ($T_3$) from Sigma (St. Louis, Mo.); B-D glucose from Calbiochem (La Jolla, Calif.); and trypsin and lima bean trypsin inhibitor from Worthington (Worthington, N.J.).

Synthetic human GHRH(1-44)NH2 was purchased from Peninsula (Belmont, Calif.) and dispensed according to the quantity specified in the vial. Recombinant human GHRH (1-44)NH2 was obtained from BioNebraska, Inc. (Lincoln, Nebr.) as a powder and weighed on an analytical balance. The concentration of stock solutions was checked spectrophotometrically and verified by quantitative amino acid analysis.

SEAP Quantitation

Assays for secreted alkaline phosphatase (SEAP) were performed using the chemiluminescent substrate in the Great Escape Detection Kit (Clontech). Culture medium was centrifuged at 14000 rpm in a microfuge centrifuge to remove cell debris. One hundred microliters of culture medium was then added to 300 ul of dilution buffer and heated at 65 C. for 30 minutes. Samples were cooled to room temperature and 100 ul of diluted sample was added to 100 ul of assay buffer. Samples were allowed to set for 5 minutes. One hundred microliters of the CSPD substrate solution was then added to each sample, incubated in the dark for 10 minutes and read on a Wallac LKB 1251 tube luminometer.

Construction of the cAMP-Responsive SEAP Reporter Vector

Figure 3:
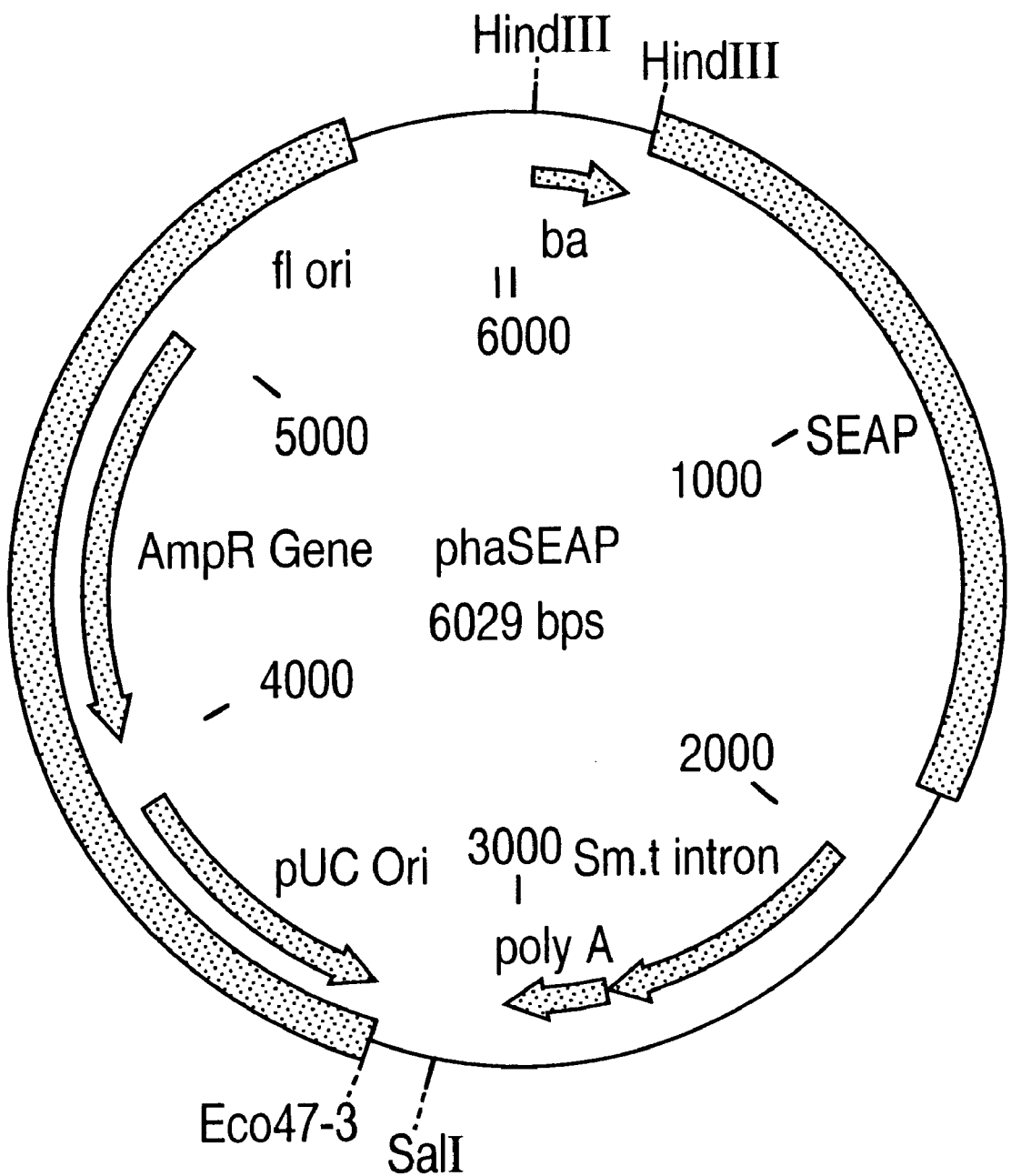
FIG. 3 is a plasmid map of phα180SEAP-Basic.

The reporter plasmid, phα180SEAP-Basic (see FIG. 3), was generated by digesting phα180A3Luc with Hind III and isolating a 230 bp human glycoprotein a subunit promoter fragment with tandem cAMP response elements on a 6% acrylamide gel. The promoter was subcloned in the sense orientation into the unique Hind III restriction site of pSEAP-Basic.

The efficacy of the cAMP-responsive promoter was evaluated by transient transfection assays using 293 and pGHRHr/293 cells. Transiently transfected 293 cells were stimulated with 1 mM 8-bromo cAMP for 20 hours, while pGHRHr/293 cells were stimulated with various concentrations of recombinant human GHRH for 6 hours. Assays for secreted alkaline phosphatase were performed using the chemiluminescent substrate in the Great Escape Detection kit.

Cotransfection of Phα180SEAP-Basic and pPur

Plasmids, phα180SEAP-Basic and pPur were cotransfected into pGHRHr/293 cells using lipofectin. Cells, $2 \times 10^5$/well in six well plates, were transfected using plasmid concentrations of 0.5 ug pPur:1 ug phα180SEAP, 1:2 and 1:1 in a total volume of 1 ml (de la Luna et al, 1988). After six hours, 1 ml of DME+20% fetal calf serum was added to the cells. Twenty four hours post-transfection, cells were subcultured 1:12 and incubated in media containing 250 ug/ml G418. Forty-eight hours post-transfection, the media was replaced with DME containing 250 ug/ml G418 and 1 ug/ml puromycin. Three weeks after transfection, stable isolates were picked using Trypsin-EDTA-treated Whatman 3MM paper and placed in 24 well culture plates. After growing cells to confluency in 150 cm$^2$ culture flasks, stable cell isolates were tested for responsiveness to recombinant GHRH(1-44)NH$_2$. Chemiluminescent-detectable alkaline phosphatase secreted in the media was quantitated using the Great Escape Detection kit.

Figure 4:
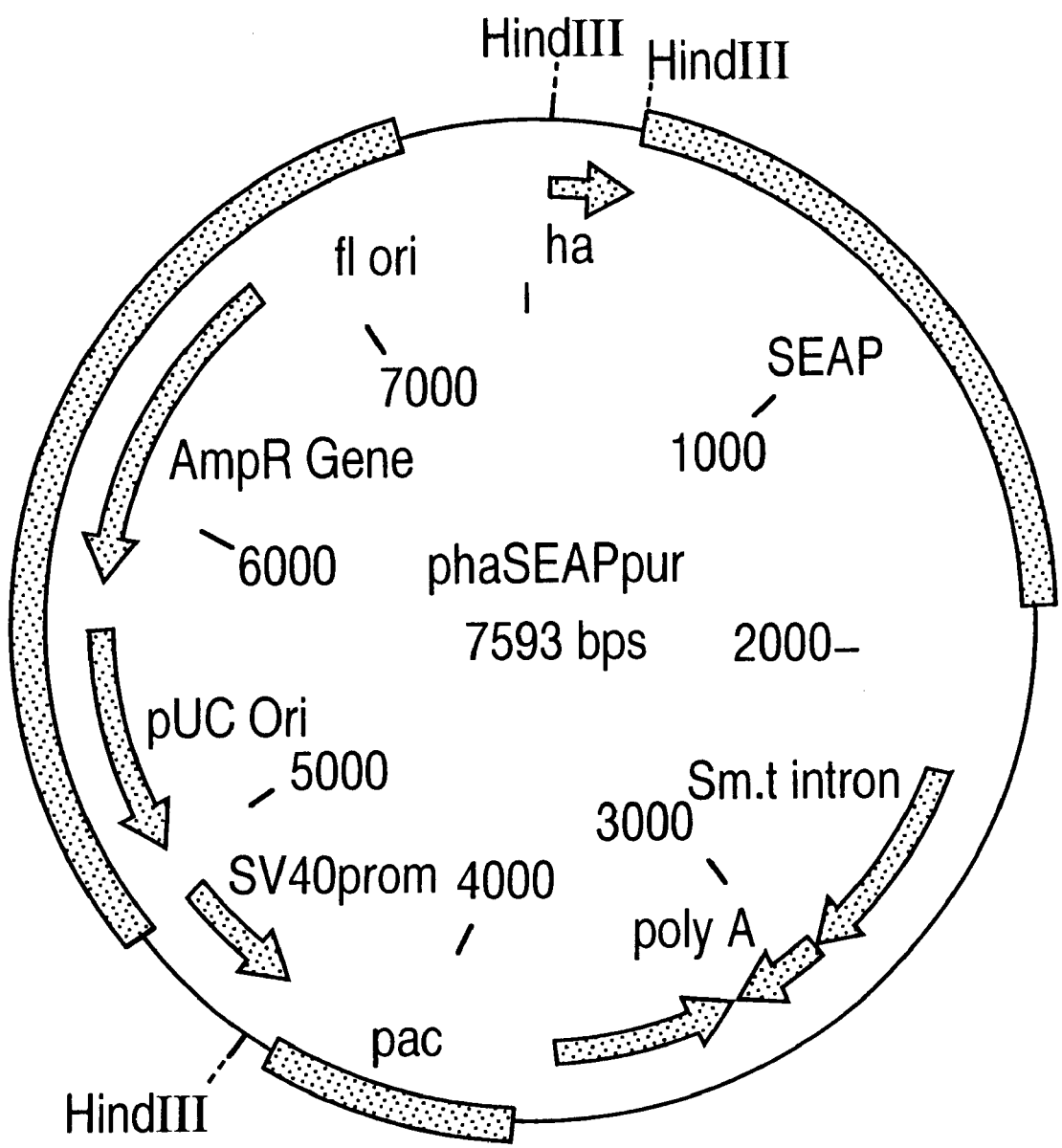
FIG. 4 is a plasmid map of phα180SEAP-Pur.

Construction of Phα180SEAPpur (FIG. 4)

The pac protein expression cassette from pPur, consisting of the SV40 early promoter, a puromycin acetyl transferase cDNA, and the SV40 early polyadenylation signal, flanked by a 5'-Pvu II site and a 3'-BamHI restriction site, was amplified and modified at the 3'-end (BamHI end) by PCR. The modifications included adding a unique Xho I restriction site to the 3'-end, as well as, insertion immediately upstream from the Xho I site of a transcriptional pause site (Eggermont and Proudfoot, 1993) in the antisense orientation relative to the pac cDNA to prevent promoter read through from the SEAP reporter construct. PCR was performed with rTth DNA polymerase and the following primers:

forward primer
5'-TAGGCTCTTCCAGCCAGCTGTGGAATGTGTG TCAG-3' [Sequence ID No. 1] and reverse primer
5'-ATTAACTCGAGGGCAGCAGGGTGTTGGGCCCTT-3' [Sequence ID No. 2].

The resulting 1700 bp PCR product was digested with Pvu II and Xho I and subcloned into the Eco47 III-Sal I restriction sites of phα180SEAP-Basic to create phα180SEAPpur. The pac expression cassette was oriented antisense relative to the SEAP expression cassette to minimize promoter occlusion (Artelt et al., 1991). The resulting plasmid was purified using the Qiagen Endotoxin Free Maxi Prep kit prior to transfection.

Stable Transfection of phα180SEAPpur Into pGHRHr/293 Cells

A stable transfection was performed in pGHRHr/293 cells using the cAMP-responsive SEAP reporter construct, phα180SEAPpur and stable transfectants were selected on the basis of puromycin resistance. phα180SEAPpur was transfected into pGHRHr/293 cells at 1, 2, 4, 8 and 16 ug/ml Opti-MEM using 8 ul of Lipofectin/ml in six well culture plates. After six hours, 1 ml of 20% fetal calf serum in DME (high glucose) was added to the cells. Twenty-four hours post-transfection the cells were subcultured 1:18 and were incubated in 250 ug/ml G418. Forty-eight hours post-transfection the media was replaced with selectable medium containing 250 ug/ml G418 and 1 ug/ml puromycin. Cells were incubated for three weeks and picked using Trypsin-EDTA treated Whatman 3MM paper and placed in 24 well plates. Upon growing stable isolates to confluency in T75 cm$^2$ culture flasks, pGHRHr/SEAP/293 cells were removed from flasks, plated in 24 well plates at 1×10$^5$ cells/well and stimulated with various doses of recombinant human GHRH (1-44)NH$_2$. Media was collected and assayed for secreted placental alkaline phosphatase. Time course studies were performed over a 20 hour period to determine the optimal time to remove media samples from the tissue cultures during stimulation with GHRH. Comparisons of synthetic and recombinant human GHRH (1-44)NH$_2$ ($10^{-13}$ to $10^{-7}$ M) were also made. Data was analyzed using FOURFIT and ALLFIT, four parameter logistic curve fitting programs.

cAMP Accumulation Assays of the pGHRHr/293 Cell Line

To demonstrate that GHRH signal transduction in pGHRHr/293 cells involves increases in intracellular cAMP and evaluate cAMP responses as a GHRH bioassay, cells were plated at 1×10$^5$ cells/well in a 24 well tissue culture plate and incubated overnight. The media was then replaced with DME containing 0.1% BSA and 0.1 mM 3-isobutyl-1-methyl-xanthine. Doses of recombinant human GHRH (1-44)NH$_2$ doses, 1×10$^{-6}$ M to 1×10$^{-12}$ M, were added and the cells were incubated for 45 minutes at 37° C. They were lysed in 60% ethanol and cAMP levels were quantitated by an immunoassay kit (Amersham). After performing the cAMP EIA, data was analyzed using Fourfit, a four parameter logistic curve fitting program.

Rat Primary Anterior Pituitary Cell Bioassay for GHRH

Rat anterior pituitary cell cultures were prepared for measuring the biological activity of GHRH, GHRH-induced release of GH was quantified using radioimmunoassay. Anterior pituitaries from fifteen female Sprague-Dawley rats were placed in a solution of Gey's media supplemented with 1% BSA, 0.25% glucose, and 0.2 mM MEM non essential amino acids at pH 7.4. Cell dispersion was performed in a solution of 400 U/ml trypsin in supplemented Gey's media for 30 minutes, 1750 KU/ml DNase-I in supplemented Gey's media for 5 minutes, and cells were triturated 15–30 times in 0.6 mg/ml lima bean trypsin inhibitor in supplemented Gey's media. Cells were filtered thru 160 u and 100 u mesh and centrifuged for 3 minutes at 1100 RPM and 12 minutes at 1600 rpm. Cell pellet was suspended at 3×10$^5$ cells/ml in DMEM supplemented with 10% fresh rat serum, 3% horse serum, 2.5% fetal calf serum, 2% Antibiotic-Antimycotic, 0.3% Fungizone, 0.45% glucose, 25 mM Hepes, 4 mM glutamine, 1 mM sodium pyruvate, 1 nM 3,3',5-triiodo-$_L$-thyronine (T$_3$), 100 nM dexamethazone and 10 uM MEM non essential amino acids. Cells were plated at 1 ml/well in 24 well plates and incubated at 8% CO2 at 37 C. for 68–72 hours. To stimulate cells with hormones, cells were washed three times in Gey's media supplemented with 1% BSA, 0.45% glucose and 25 mM Hepes. GHRH (1-44) NH$_2$ was added to cells in 1 ml of supplemented Gey's media and cells were incubated for 3 hours before collecting media. Rat growth hormone levels were quantitated using a radioimmunoassay kit (Amersham).

Statistics and Curve Fitting

Sigmoidal dose response curves were fit by four parameter logistic curve fitting using FOURFIT (Grotjan and Steinberger, 1977), with multiple curves being compared using ALLFIT (DeLean et al.,1978). Variances in the response of the rat pituitary bioassay were homogeneous and thus curves were fit using an unweighted regression analysis. For cAMP and SEAP bioassays, a weighted regression analysis was performed with weights assigned as the reciprocal of predicted variance. Predicted variances were fit by regression analysis using a locally prepared copy of PREFIT which yielded the following equations: Predicted variance in cAMP responses=$0.041 \times (Y)^{1.89}$. Predicted variances in SEAP responses=$0.32 \times (Y)^{1.54}$.

Results

Optimization of Lipofectin-Mediated Transfection

To determine optimal conditions for transfection, 293 cells were transiently transfected with various concentrations of pha180SEAP and lipofectin and stimulated with various doses of 8-bromo cAMP. Media was collected 20 hours later for measurement of chemiluminescent-detectable alkaline phosphatase. The maximum amount of cAMP-induced SEAP expression occurred when cells were transfected with 8 ul of lipofectin and 8 ug of phaSEAP (data not illustrated).

Figure 5:
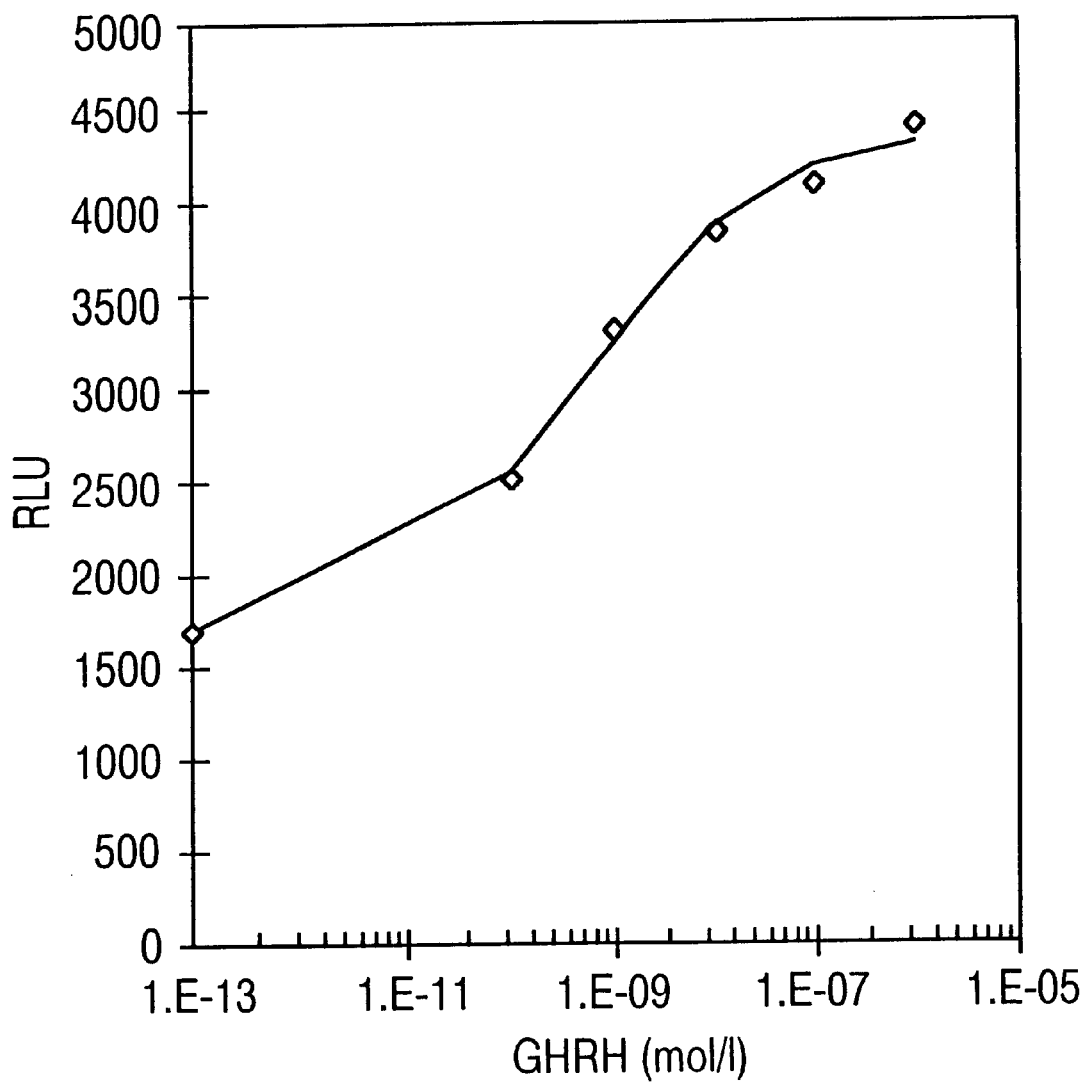
FIG. 5 is a graph showing GHRH induced expression of reporter protein.

Evaluation of the cAMP-responsive Secreted Alkaline Phosphatase Construct, pha180SEAP, as a Reporter System The ability of GHRH to stimulate the expression of the SEAP reporter cDNA was evaluated using pGHRHr/293 cells transiently transfected with pha180SEAP. Cells were incubated with various doses of GHRH(1-44)NH$_2$ ($10^{-10}$ to $10^{-6}$ M) for 6 hours and media was then assayed for SEAP activity. Under these conditions, GHRH induced a 2.5 fold increase in the expression of the reporter protein with an ED$_{50}$ of $5.1 \times 10^{-10}$ M (FIG. 5). These data suggested that the cAMP-response element in the human a promoter could be used to drive the expression of the SEAP reporter gene in response to increasing doses of GHRH.

Construction of a Stable GHRH Receptor/SEAP Reporter Cell Line

Two methods for the construction of the pGHRHr/SEAP/293 cell line were evaluated. Cotransfection of a pha180SEAP and pPur was initially performed. Although several stable cell lines resistant to 1 ug/ml puromycin and 250 ug/ml G418 were isolated, none exhibited an increase in SEAP activity when stimulated with recombinant human GHRH. Thus, we constructed pha180SEAPpur to more effectively isolate cells with the reporter system.

Transfection of pGHRHr/293 cells with pha180SEAPpur, yielded 20 stable isolates resistance to both puromycin and G418. Each stable isolate responded to recombinant human GHRH with a dose dependent increase in SEAP activity. One clonal cell line, pGHRHr/SEAP/293 #815-4 was characterized in further detail as a potential for a GHRH bioassay.

Figure 6:
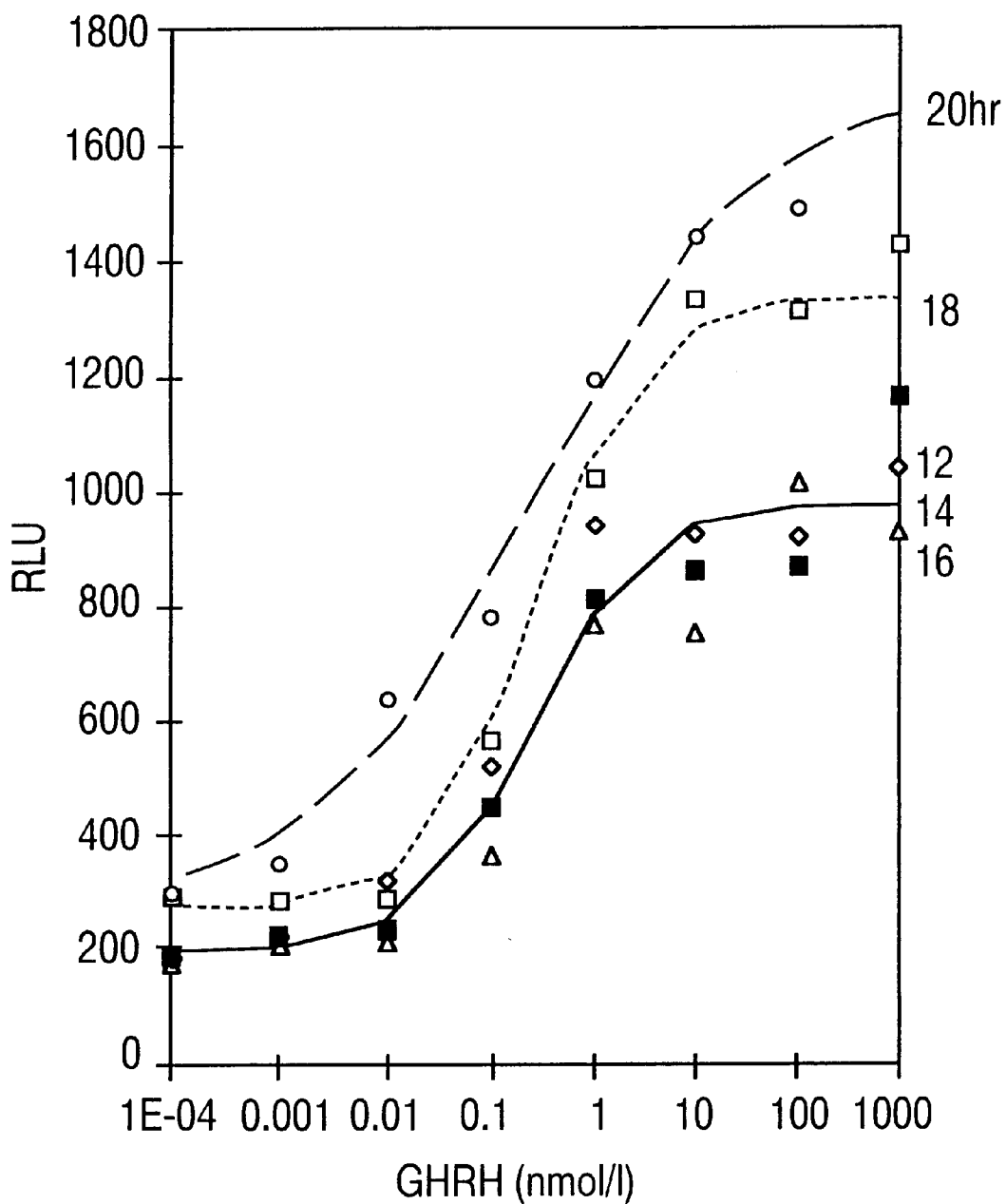
FIG. 6 is a graph showing a time course of GHRH induced expression of the reporter protein.

Time course studies were performed to determine the optimal from addition of GHRH to collection of medium for measurement of SEAP activity. Incubation periods of 2, 4, or 8 hours yielded minimal increases in SEAP expression which was sub-optimal for analyzing dose response relationships (data not shown). Between 12 and 18 hours, GHRH induced a 4.8-fold increase in SEAP activity (FIG. 6). The calculated ED$_{50}$'s for dose-response curves after 12, 14, 16 and 18 hours of exposure to recombinant GHRH were not found to be significantly different ($2.61 \times 10^{-10}$ M). At 18 and 20 hours the SEAP activity increased 1.3 and 1.7 fold, respectively over the 12–16 hour time points. However, a 20 hour GHRH exposure yielded a dose response curve with a lower slope, indicating that the most appropriate time frame to remove the media was between 12–16 hours after the addition of GHRH. For all subsequent assays, a 16 hour incubation time was used.

Validation Against Conventional Bioassays for GHRH

Figure 7:
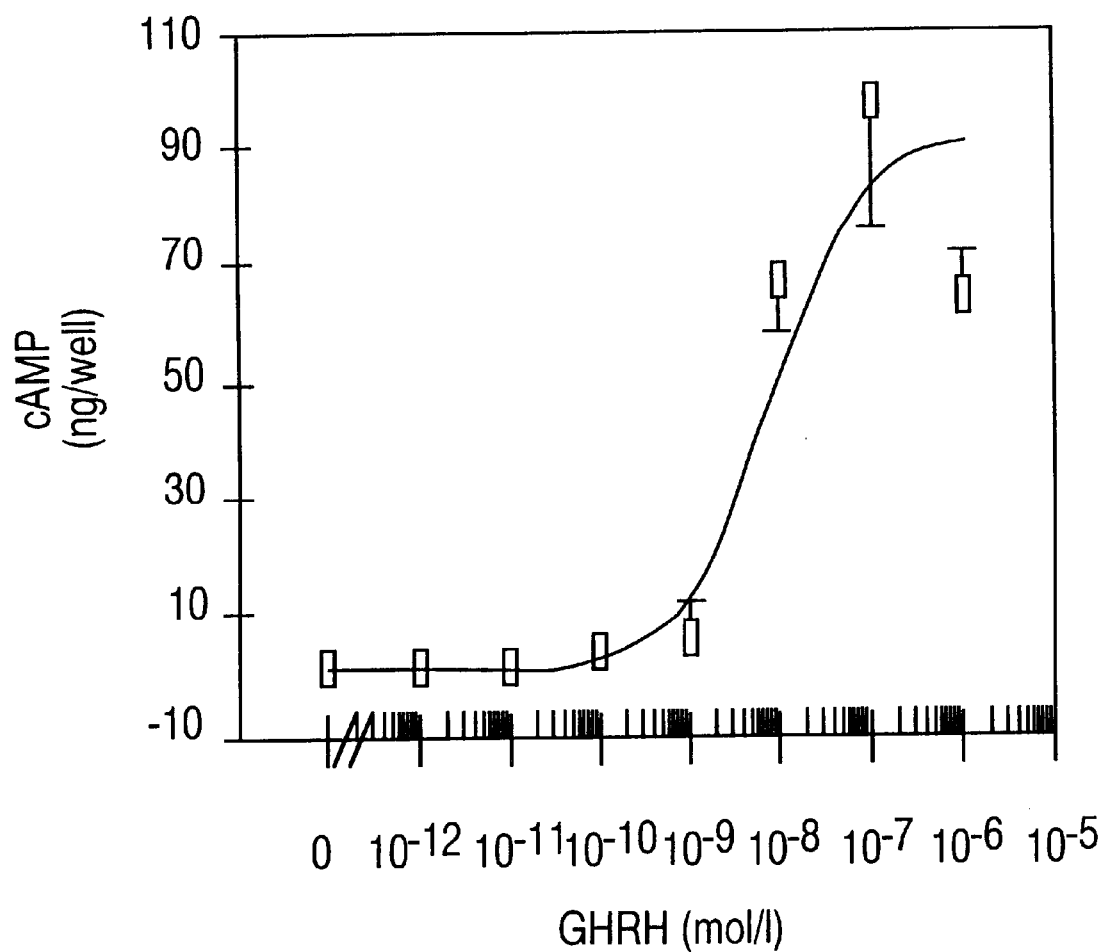
FIG. 7 is a graph showing recombinant GHRH induced cAMP concentration.

To verify human GHRH evokes an increase in intracellular cAMP and evaluate cAMP responses as a potential bioassay, pGHRHr/293 cells were stimulated with various doses of recombinant human GHRH (1-44)NH$_2$ ($10^{-12}$ to $10^{-6}$ M) for 45 minutes. Recombinant human GHRH(1-44) NH$_2$ elicited a dose-dependent increase in intracellular cAMP concentration in 293 cells stably expressing the porcine GHRH receptor with a calculated ED50 of $8.4\pm3.6\times10^{-9}$ M (FIG. 7).

Figure 8:
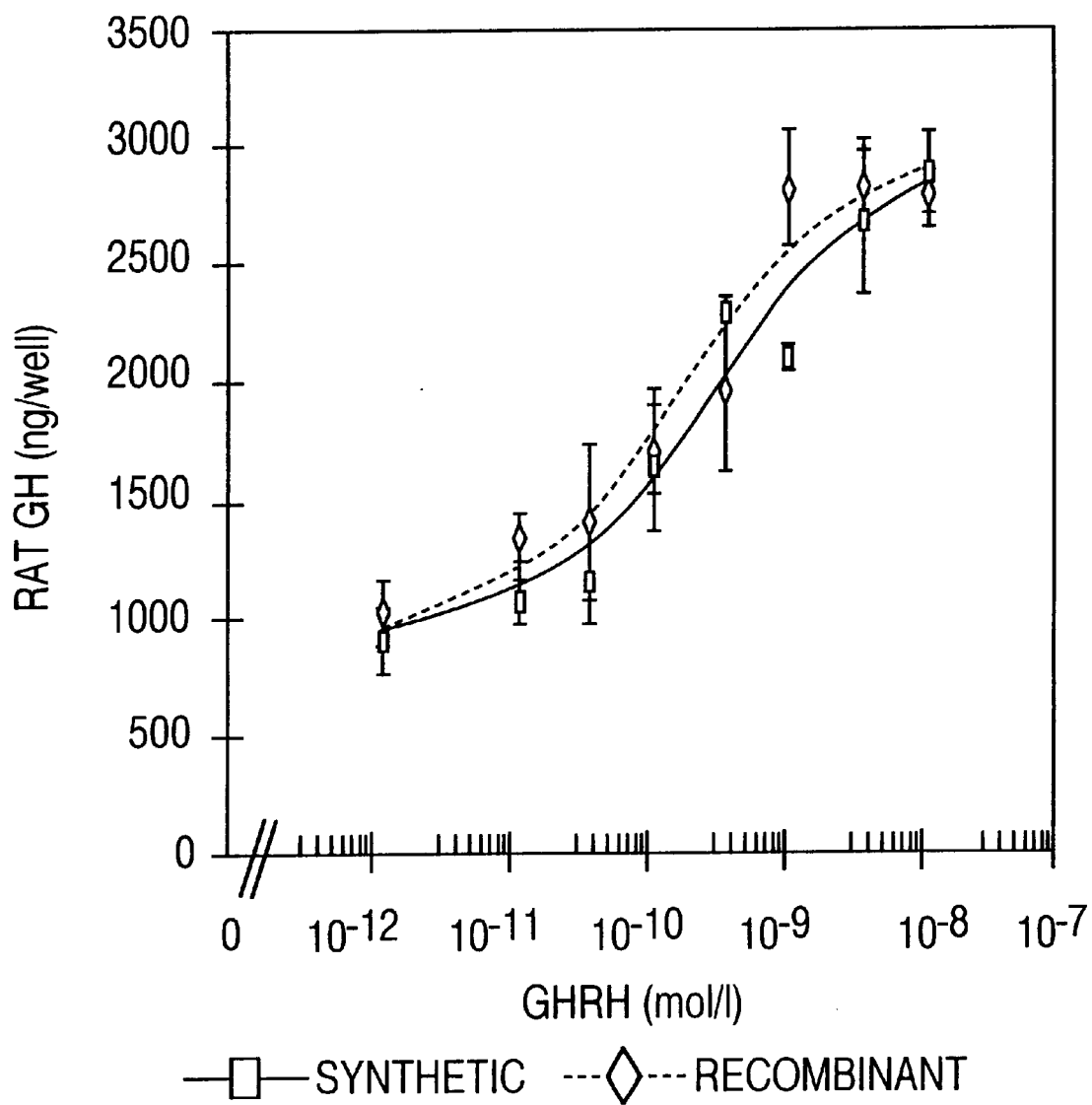
FIG. 8 is a graph showing GHRH induced GH secretion.

To validate the pGHRHr/SEAP/293 cell bioassay, the conventional GHRH bioassay using primary rat pituitary cell cultures was used to assay synthetic and recombinant GHRH $(1-44)NH_2$. Synthetic and recombinant human GHRH $(1-44)NH_2$ induced a 3.1-fold increase in GH secretion into the medium with respective $ED_{50}$ values of $3.64\pm1.76\times10^{-10}$ M and $2.16\pm1.04\times10^{-10}$ M (FIG. 8). In this bioassay, recombinant GHRH was $1.69\pm0.67$ times as potent as synthetic GHRH. The dose response curves generated using the rat pituitary bioassay suggest that recombinant human GHRH$(1-44)NH_2$ has a similar biologically potency to synthetic human GHRH$(1-44)NH_2$ reference preparation. However, the standard error of the potency estimates in the primary pituitary assay is relatively large, because of the inherent variability in this assay.

Figure 9:
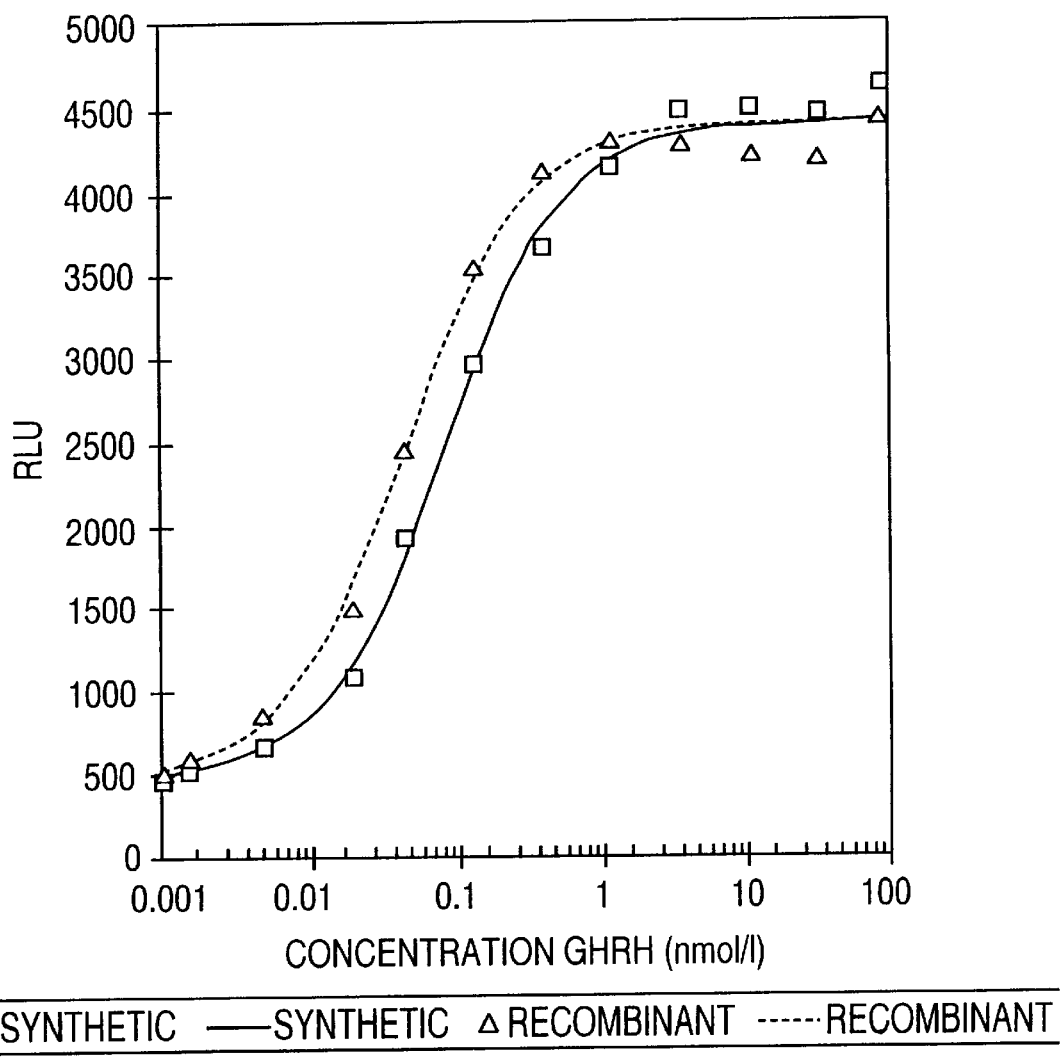
FIG. 9 is a graph showing GHRH induced SEAP expression.

In an analogous experiment comparing synthetic and recombinant human GHRH $(1-44)NH_2$, pGHRHr/SEAP/293 cells responded with a 9.1-fold increase in SEAP expression (FIG. 9). The minimal detectable dose was $1.47\times10^{-12}$ M synthetic GHRH. The calculated $ED_{50}$'s for synthetic and recombinant GHRH were $7.78\pm0.52\times10^{-11}$ M and $4.26\pm0.28\times10^{-11}$ M, respectively.

In the pGHRHr/SEAP/293 reporter bioassay, recombinant GHRH was $1.83\pm0.13$ times as potent as synthetic GHRH ($p<0.0001$). Thus, the relative potencies obtained in the two bioassays were similar, but the pGHRHr/SEAP/293 reporter bioassay was more sensitive, more responsive and had less inherent error than the pituitary cell culture bioassay. Further, the pGHRHr/SEAP/293 reporter bioassay can be performed more rapidly and at a lower cost.

Discussion

The assessment of hormonal activity is most appropriately performed by biological assays which measure specific responses. Although bioassays using tissues such as rat anterior pituitary cell cultures yield specific biological responses, they are tedious, expensive, and inherently variable. The ability to clone and express cDNA's for hormone receptors has facilitated the development of new bioassays which are equally specific, but less tedious to perform and have inherently lower error in the quantitation of responses.

As noted in the introduction, GHRH receptors are members of the G-protein receptor family which use cyclic AMP as a second messenger. One of the most important criteria in the construction of the bioassay was to demonstrate that human GHRH was capable of eliciting a dose dependent increase in cAMP in 293 cells expressing the porcine GHRH receptor. Human GHRH$(1-44)NH_2$ differs from porcine GHRH by only three amino acids in a region of the C-terminus, which has been determined to be nonessential for biological activity (Bohlen et al., 1983). The human GHRH receptor shares 85% sequence homology to the porcine receptor. Thus, we hypothesized that porcine GHRH would respond appropriately to human GHRH.

The receptor-reporter bioassay for GHRH described herein exploits the cAMP-second messenger system. This signal transduction pathway is reasonably well understood and characterized. Intracellular increases in cAMP in pGHRHr/SEAP/293 cells can be used as a bioassay for GHRH, but the assay is one-fold less sensitive than the rat pituitary cell bioassay and is also a tedious procedure involving cell extractions which increase the assay variance. After establishing that human GHRH could elicit a dose dependent increase in cAMP in the pGHRHr/293 cell line, the means for implementing a straight forward reporter bioassay were devised.

Previously reported bioassays for human gonadotropins had utilized the luciferase reporter gene (Albanese et al., 1994; Jia et al., 1993). The alkaline phosphatase reporter system was selected over luciferase, B-galactosidase and chloramphenicol acetyl transferase reporter systems, because alkaline phosphatase is secreted into the culture medium. This was accomplished by inserting a translational terminator after amino acid 489 of the native protein resulting in the elimination of 24 amino acids at the C-terminus of the protein, permitting efficient secretion of the protein into the culture fluid (Berger et al., 1988). This eliminates cell lysis and extraction steps characteristic of the previously mentioned reporter systems, both which take time and increase variability in responses.

One important component of the reporter plasmid, was the ha180 cAMP-responsive promoter with tandem cAMP response elements which was subcloned upstream of the SEAP expression cassette. It then became important to demonstrate that cAMP and GHRH receptor interactions were capable of driving the expression of the SEAP gene. This was accomplished in transient transfections of the pGHRHr/293 cell line which demonstrated a dose dependent increase in SEAP expression.

A major concern when developing a stable reporter cell line involves the long term stability of the genes of interest in the genome of the transfected cell line. Selectable markers provide a means to generate stable cell lines by recombination of the foreign genes into the genome. Only cells which confer resistance to an antibiotic are sustained in culture. In the past literature, examples of utilizing cotransfection of the reporter plasmid, the receptor plasmid and a plasmid conferring resistance to a particular antibiotic have been used. This technique works, but does not provide a specific marker for either the reporter or receptor gene. A recombinant reporter or receptor gene could be excised from the genome, leaving the gene conferring antibiotic resistance, thus making the cell line appear stable. The approach used herein utilizes two independent selectable markers for each gene to be expressed, each which have been subcloned into the corresponding plasmid. Resistance to G418 marks the presence of the receptor gene and resistance to puromycin marks the presence of the reporter gene. Thus, selective pressure is maintained for both expression of the receptor and the reporter genes.

In comparison to the conventional rat pituitary bioassay, the pGHRHr/SEAP/293 cell line provides an accurate and easy method for measuring the biological activity of GHRH. The sensitivity of the pGHRHr/SEAP/293 cell line is nearly 10-fold higher than the pituitary bioassay and the standard errors are significantly reduced. The potency estimates of the recombinant vs. the synthetic preparations of GHRH were nearly the same in the two assays, illustrating the strong similarities in response mechanisms in each assay. Thus, the pGHRHr/SEAP/293 cell line provides a precise and efficient tool for measuring the potency of GHRH.

We claim:

1. An assay system for detecting growth hormone releasing hormone (GHRH) activity in a sample, the assay system comprising a cell which comprises:
   (a) a cAMP-responsive promoter;
   (b) a nucleic acid sequence encoding a reporter and operatively connected to the cAMP-responsive promoter; and
   (c) a nucleic acid sequence encoding a GHRH-responsive protein; wherein expression of the reporter correlates with GHRH activity of the sample and wherein the assay system is approximately ten times more sensitive for detecting GHRH activity than a pituitary cell culture bioassay.

2. The assay system of claim 1 wherein the sample is human.

3. The assay system of claim 1 wherein the GHRH-responsive protein is porcine GHRH receptor.

4. The assay system of claim 1, wherein the cAMP responsive promoter is human glycoprotein hormone alpha promoter, and the reporter is alkaline phosphatase.

5. The assay system of claim 1, wherein the nucleic acid sequence encoding the reporter further comprises a nucleic acid sequence encoding a selectable marker.

6. The assay system of claim 5, wherein the sample is human GHRH.

7. The assay system of claim 5, wherein the GHRH-responsive protein is porcine GHRH receptor.

8. The assay system of claim 5, wherein the cAMP responsive promoter is human glycoprotein hormone alpha promoter, and the reporter is alkaline phosphatase.

9. The assay system of claim 8, wherein the sample is human.

10. The assay system of claim 8, wherein the GHRH-responsive protein is porcine GHRH receptor.

11. A recombinant cell, comprising:
   (i) a human glycoprotein hormone alpha promoter;
   (ii) a nucleic acid sequence encoding a selectable marker and encoding an alkaline phosphatase reporter operatively connected to the human glycoprotein hormone alpha promoter; and
   (iii) a nucleic acid sequence encoding a porcine GHRH receptor, wherein binding of said receptor by GHRH or an agonist thereof results in said receptor activating the production of cAMP.

12. A method for detecting growth hormone releasing hormone (GHRH) activity in a sample, the method comprising:
   (a) contacting a recombinant cell with the sample, the recombinant cell comprising:
      (i) a nucleic acid sequence encoding a selectable marker and encoding a reporter operatively connected to a cAMP-responsive promoter; and
      (ii) a nucleic acid sequence encoding a GHRH-responsive protein; and
   (b) measuring the expression of the reporter, wherein the expression of reporter indicates the presence of GHRH activity in the sample.

13. The method of claim 12, wherein the sample is human.

14. The method of claim 12, wherein the GHRH-responsive protein is porcine GHRH receptor.

15. The method of claim 12 wherein the cAMP responsive promoter is human glycoprotein hormone alpha promoter, and the reporter is alkaline phosphatase.

16. The method according to claim 12, wherein the cAMP responsive promoter is human glycoprotein hormone alpha promoter, and the reporter gene is alkaline phosphatase.

* * * * *